United States Patent
Bos et al.

(10) Patent No.: US 10,499,803 B2
(45) Date of Patent: Dec. 10, 2019

(54) VOCAL CORD STROBOSCOPY

(71) Applicant: KARL STORZ Imaging, Inc., Goleta, CA (US)

(72) Inventors: Pieter Henderikus Andries Bos, Tuttlingen (DE); Timothy King, Goleta, CA (US)

(73) Assignee: KARL STORZ Imaging, Inc., Goleta, CA (US)

( * ) Notice: Subject to any disclaimer, the term of this patent is extended or adjusted under 35 U.S.C. 154(b) by 77 days.

(21) Appl. No.: 15/814,779

(22) Filed: Nov. 16, 2017

(65) Prior Publication Data
US 2019/0142264 A1 May 16, 2019

(51) Int. Cl.
| A61B 1/00 | (2006.01) |
| A61B 1/267 | (2006.01) |
| G10L 25/27 | (2013.01) |
| H04N 5/232 | (2006.01) |
| H04N 5/225 | (2006.01) |
| A61B 1/045 | (2006.01) |
| A61B 7/02 | (2006.01) |
| A61B 1/06 | (2006.01) |

(Continued)

(52) U.S. Cl.
CPC ........ *A61B 1/2673* (2013.01); *A61B 1/00006* (2013.01); *A61B 1/00009* (2013.01); *A61B 1/00045* (2013.01); *A61B 1/045* (2013.01); *A61B 1/06* (2013.01); *A61B 1/0684* (2013.01); *A61B 1/233* (2013.01); *A61B 7/023* (2013.01); *G10L 25/27* (2013.01); *H04N 5/2256* (2013.01); *H04N 5/23216* (2013.01); *H04N 5/23293* (2013.01); *A61B 7/008* (2013.01);

*G10L 25/66* (2013.01); *G10L 2025/903* (2013.01); *H04N 2005/2255* (2013.01); *H04R 1/028* (2013.01)

(58) Field of Classification Search
CPC ..... A61B 1/267; A61B 1/2673; A61B 1/2676; A61B 1/04
See application file for complete search history.

(56) References Cited

U.S. PATENT DOCUMENTS

| 8,540,626 B2 | 9/2013 | Seto |
| 8,550,990 B2 | 10/2013 | Seto |

(Continued)

FOREIGN PATENT DOCUMENTS

| JP | 2014124331 A | 7/2014 |
| JP | 2015016096 A | 1/2015 |

(Continued)

OTHER PUBLICATIONS

Bradley, Synchronization and rolling shutter compensation for consumer video camera arrays, University of British Columbia, 8 pages.

(Continued)

*Primary Examiner* — Julianna N Harvey
*Assistant Examiner* — Christina Negrellirodriguez
(74) *Attorney, Agent, or Firm* — Michael J. Loi

(57) ABSTRACT

A system, method, scope device, and camera control module device for a stroboscopic laryngoscope, to enable scopes able to operate with a rolling shutter-type image sensor. With selected pulsing of a strobe light, subset image data from adjacent rolling-shutter frames is selected, gain compensated for missing light and combined into a new single video frame.

15 Claims, 4 Drawing Sheets

(51) Int. Cl.
  *A61B 1/233* (2006.01)
  *H04R 1/02* (2006.01)
  *A61B 7/00* (2006.01)
  *G10L 25/90* (2013.01)
  *G10L 25/66* (2013.01)

(56) References Cited

U.S. PATENT DOCUMENTS

| | | |
|---|---|---|
| 2012/0016200 A1 | 1/2012 | Seto |
| 2012/0016201 A1 | 1/2012 | Seto |
| 2013/0113970 A1* | 5/2013 | Laser ................ A61B 1/00052 348/308 |
| 2016/0073865 A1 | 3/2016 | Takashi |

FOREIGN PATENT DOCUMENTS

| | | |
|---|---|---|
| JP | 2015019697 A | 2/2015 |
| WO | 2014134501 A2 | 9/2014 |
| WO | 2015004975 A1 | 1/2015 |

OTHER PUBLICATIONS

European Search Report, Munich, Germany, Apr. 12, 2019; Application No. 18206697.7-1124.

\* cited by examiner

VOCAL CORD STROBOSCOPY

TECHNICAL FIELD OF THE INVENTION

The invention relates generally to the field of medical imaging scopes and more specifically to stroboscopes for examining vocal cords.

BACKGROUND OF THE INVENTION

Video stroboscopy is a medical examination procedure that combines video observation and display with a specially timed illumination to evaluate the function of the vocal cords, or larynx. During vocalization such as speech and singing, the vocal folds in the larynx vibrate too rapidly to discern the movement under constant lighting conditions. Stroboscopy solves this problem by using a strobe light to illuminate the larynx. The strobe light emits light flashes at a rate either matched with or very slightly different than the vibration base frequency of the vocal folds, causing the folds to appear to move in slow motion when viewed through the scope. An examiner may then observe the movement and function of the larynx as a patient makes particular sounds.

Such stroboscopic rhino laryngoscopy exams are typically performed with either a flexible endoscope passed through the nose. The endoscope used may also be called a stroboscopic laryngoscope, with the procedure referred to as laryngeal stroboscopy. The scope contains an optical system and a small camera for observation and recording of the exam for later review.

In existing systems, the process of laryngeal stroboscopy typically requires a global exposure type shutter arrangement for the scope camera, with the strobe light exposing the entire image sensor array at the desired position of the vocal cords during vibration. However, rolling shutter type image sensors arrays, including many CMOS image sensors, may offer higher resolution capabilities at a comparably cheaper price point to global shutter type imaging arrays. Further, the use of rolling shutter type arrays such arrays in laryngeal stroboscopy would allow interoperability of designs across existing scope platforms, reduce costs, and enhance capabilities of scopes.

What is needed, therefore, are improved systems and techniques for laryngeal stroboscopy that enable better use of rolling shutter type image sensors in scopes.

SUMMARY OF THE INVENTION

It is an object of the invention to provide improved ability to perform stroboscopic laryngoscope examinations with rolling shutter type scope cameras. It is a further object of the invention to improve the processing of data received from such scope cameras. In order to achieve these objects, various aspects of the invention provide a system, method, scope device, and camera control module device for a stroboscopic laryngoscope, to enable scopes able to operate with a rolling shutter-type image sensor. With selected pulsing of a strobe light, subset image data from adjacent rolling shutter frames is selected and combined into a new single video frame.

According to a first aspect of the invention, a system is provided for examining vocal cords. The system includes a stroboscopic laryngosocope, a microphone, and a camera control unit (CCU) including an electronic controller communicatively coupled to the stroboscopic laryngoscope and the microphone. A display device is communicatively coupled to the CCU for displaying video to the operator. The CCU electronic controller is operable for measuring a patient's vocalization with the microphone and determining a base frequency of the vocalization. During the patient's vocalization, the CCU controls the pulsing of a light emitter associated with stroboscopic laryngoscope at a timing interval selected based on the base frequency of the vocalization. The CCU also controls the process of reading image data from an image sensor array of the stroboscopic laryngoscope according to a rolling shutter scheme including: (a) creating two or more light emitter pulses during first and second adjacent image frames, (b) reading the image data from lines of the image sensor array offset in time such that at least two of the two or more light emitter pulses each expose sensor pixels in both first and a second image frames simultaneously, and (c) selecting a first subset of the image data from the first frame and a second subset of the image sensor data from the second frame, the second subset including a different frame portion than the first subset, the first and second subsets including data resulting from the simultaneous exposure of the first and second frames. The CCU combines the image data from the first and second subsets to create a combined image frame based on the first and second frames for display.

According to a second aspect of the invention, a method is provided for operating a medical scope system. The method includes measuring a patient's vocalization with a microphone and determining a base frequency of the vocalization. The method observes the patient's vocal cords with a stroboscopic laryngoscope during the patient's vocalization and pulsing a light emitter of the stroboscopic laryngoscope at time intervals selected based on the base frequency of the vocalization. While doing so, the method includes reading image data from an image sensor array of the stroboscopic laryngoscope according to a rolling shutter process including: (a) creating two or more light emitter pulses during two consecutive video frames, (b) reading the image data from lines of the image sensor array offset in time such that at least two of the two or more light emitter pulses each expose sensor pixels in both first and second adjacent frames simultaneously, and (c) selecting a first subset of the image sensor data from the first frame and a second subset of the image sensor data from the second frame, the second subset including a different frame portion than the first subset, the first and second subsets including data resulting from the simultaneous exposure of the first and second frames. The method combines the image sensor data from the first and second subsets to create a combined frame based on the first and second frames.

According to a third aspect of the invention, a CCU is provided for use with a stroboscopic laryngoscope. The CCU includes an electronic controller adapted to communicatively couple to a stroboscopic laryngoscope, a display device, and a microphone. The CCU electronic controller is operable for receiving an audio signal patient's vocalization with the microphone and determining a base frequency of the vocalization. It commands a light emitter of the stroboscopic laryngoscope or a CCM associated with the stroboscopic laryngoscope to pulse at time intervals selected based on the base frequency of the vocalization. The CCU reads image data from an image sensor array of the stroboscopic laryngoscope according to a rolling shutter process including: (a) creating two or more light emitter pulses during two consecutive video frames, (b) reading the image data from lines of the image sensor array offset in time such that at least two of the two or more light emitter pulses each expose sensor pixels in both first and second adjacent frames simultaneously, and (c) selecting a first subset of the image sensor data from the first frame and a second subset of the image sensor data from the second frame, the second subset including a different frame portion than the first subset, the first and second subsets including data resulting from the simultaneous exposure of the first and second frames. Then the CCU combines the image sensor data from the first and second subsets to create a combined frame based on the first and second frames.

According to a fourth aspect of the invention, a system is provided for processing video of a stroboscopic laryngoscope. The system includes an exposure controller that is configured to generate a pulse signal for a light source at a timing interval based on a frequency of the vocalization, the pulse signal including two or more pulses during first and second adjacent image frames of a video stream. The system is configured to receive data from an image sensor with a rolling shutter that receives lines of image data to form the image frames during vocalization, the image sensor receiving the lines such that at least two of the two or more pulses each expose sensor pixels in both the first and second image frames simultaneously. The system also includes an image processor that is configured to select a first subset of the image data from the first image frame and a second subset of the image data from the second image frame, the second subset including a different frame portion than the first subset, the first and second subsets including data resulting from the simultaneous exposure of the first and second frames, and that combines the image data from the first and second subsets to create a combined image frame.

In some embodiments of the fourth aspect, the system may include a gain processing module that is configured to apply a digital gain to values on one or more lines in the first and second subsets to compensate for a loss of exposure due to a time gap between the first and second adjacent frames.

The invention may also be embodied as a tangible, non-transitory computer readable medium such as a flash storage drive or hard drive carrying program code executable by electronic processors of a CCU for performing the steps herein.

In some implementations of the various aspects of the invention, the first subset includes only data scanned in a second-half period of reading the first frame, and the second subset includes only data scanned in a first-half period of reading the second frame.

In some implementations of the various aspects of the invention, the functionality or process includes applying a digital gain to values on one or more lines in the first and second subsets to compensate for a loss of exposure due to a gap time between the first and second frames in the rolling shutter process.

In some implementations of the various aspects, the functionality or process includes repeating (a)-(c) for subsequent pairs of image frames following the first and second image frames and combining image data from subsequent first and second subsets into subsequent combined image frames. It may also includes creating subsequent sequences of two or more light emitter pulses for subsequent image frames spaced in time from the pulses of the first and second image frames according to integer multiples of a time period that is the inverse of the base frequency of the vocalization.

In some implementations of the various aspects, the functionality or process includes creating the two or more light emitter pulses in a sequence in which the pulses are spaced at a time period that is the inverse of the base frequency of the vocalization, and in which a gap occurs in the sequence such that at least one pulse is partly or completely missing in order to fully expose image sensor array lines for producing the two subsets. This leads to the fact that certain parts of the image sensor array are less exposed in comparison to other parts that are fully exposed.

These and other features of the invention will be apparent from the following description of the preferred embodiments, considered along with the accompanying drawings.

BRIEF DESCRIPTION OF THE DRAWINGS

The present invention will become more fully understood from the detailed description given herein and the accompanying drawings which are given by way of illustration only, and thus are not limitative of the present invention, and wherein.

DETAILED DESCRIPTION OF EXAMPLE EMBODIMENTS

The present invention provides a system, method, scope device, and camera control module device for a stroboscopic laryngoscope to enable scopes able to operate with a rolling shutter-type image sensor. With selected pulsing of a strobe light, subset image data from adjacent rolling-shutter frames is selected and combined into a new single video frame.

Figure 1:
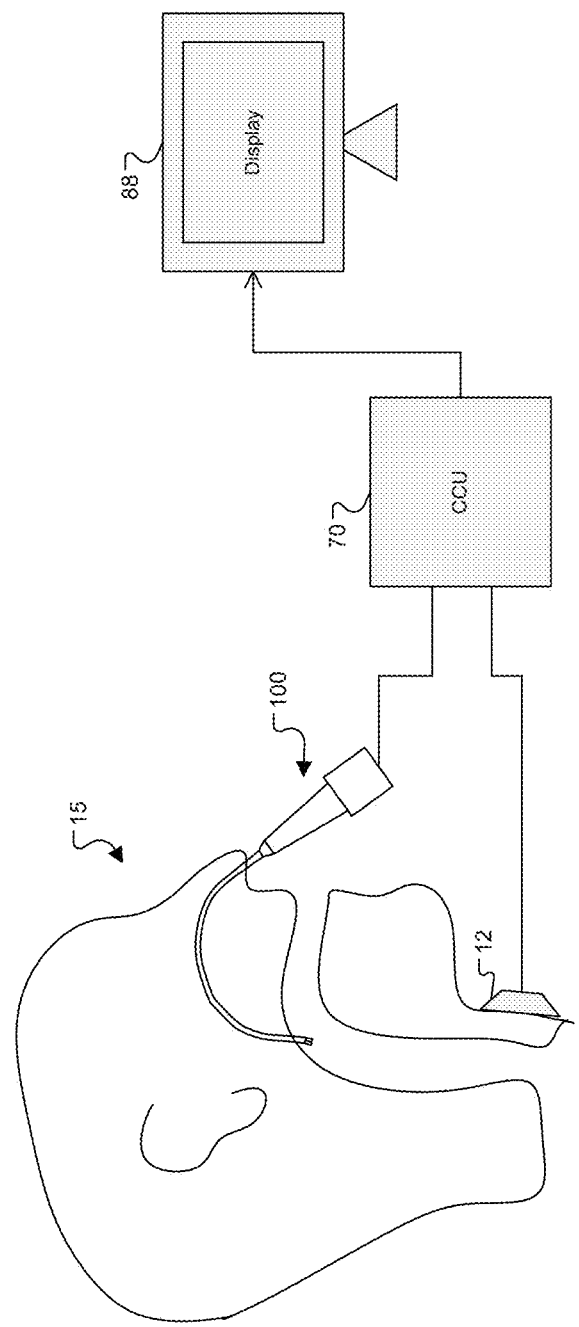
FIG. 1 is diagram showing set up of a medical stroboscopy system.

FIG. 1 is a diagram showing the set up of a medical stroboscopy system according to an example embodiment. To conduct an examination, the patient 15 preferably has a microphone 12 attached to their throat near the larynx, or mounted at a suitable location for detecting the patient's vocalizations during the exam, such as speech and singing certain tones as requested by the examiner. The diagram shows a flexible stroboscopic laryngoscope 100 passed through the patient's nose to point down the throat toward the larynx and vocal cords. Rigid or flexible scopes may instead be passed through the mouth to achieve a similar viewing angle. The scope 100 and microphone 12 are both connected to a camera control unit (CCU) 70 by cables, typically digital data transmission cables, which may also provide power. CCU 70 sends control commands to the scope and receives image data from the scope and audio data or signaling from the microphone.

The CCU has the capability to detect the base frequency of the vocal cord in order to generate a frequency for the LED light source, which is in phase with the audio frequency of the vocal cord. The camera can be a proximal head, rigid endoscope or flexible videoendoscope with a rolling shutter sensor used for medical purposes in the endoscopy. The CCU can also be built of sub modules, where for example the display or light source are separated modules. The data communication link functionality of the CCU may be separated into a link module that communicates with the scope device, while the image processing functionality may be included in a camera control module of the CCU.

Figure 2:
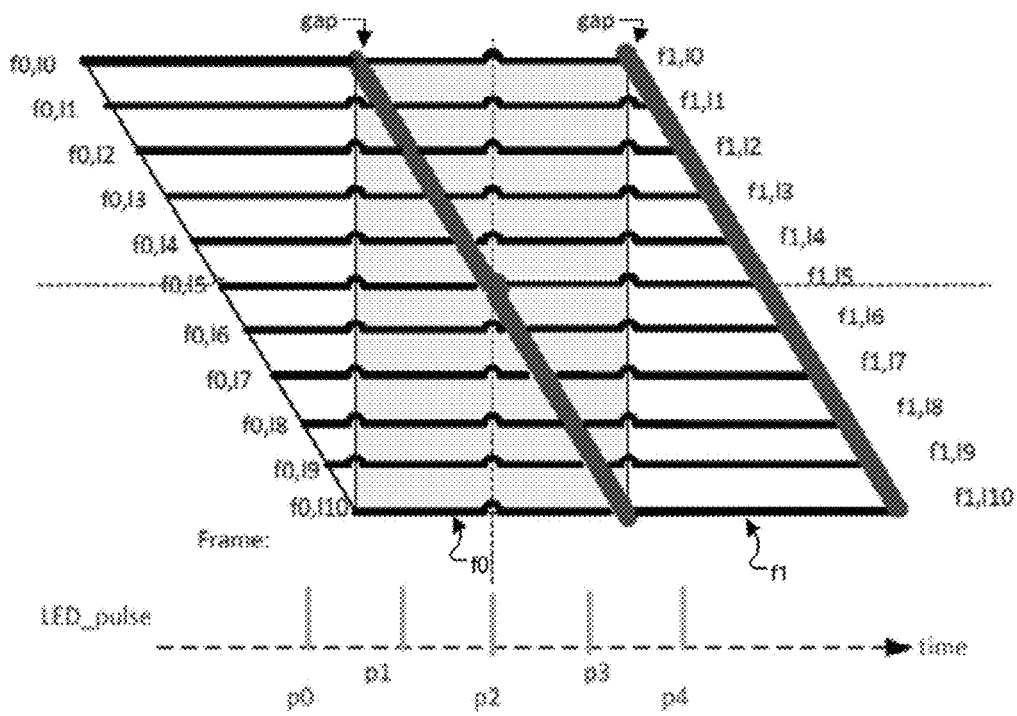
FIG. 2 and FIG. 3 show timing diagrams for a process of strobing the light source and reading the image sensor array with a rolling shutter.
Figure 3:
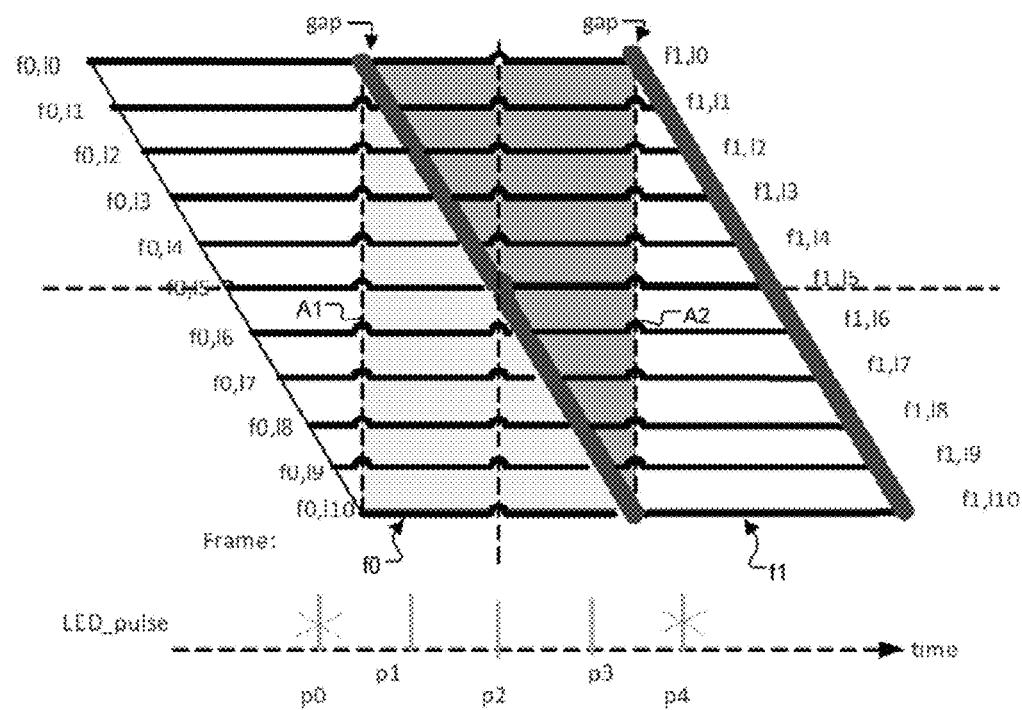

FIG. 2 and FIG. 3 show timing diagrams for a process of strobing the light source and reading the image sensor array with a rolling shutter. According to an example embodiment, the system generates video frames according to a rolling shutter concept as shown. The timing diagram of FIG. 2 shows the pulses p0-p4 of the scope light emitter LED (LED_pulse time axis) as it relates to the reading of sensor array lines L0-L10 according to a rolling shutter scheme. The number of lines depends on the vertical resolution of the image sensor and is not limited to 10 lines. The diagram shows two frames f0 an f1 which are exposed with the LED pulses p0-p3. The pulses expose lines being scanned in both depicted frames, f0 and f1, because the lines are scanned beginning at different times according to a rolling shutter scheme. The use of the scanned data is described further below. As shown in FIG. 2 and FIG. 3, the diagrams include two frames f0 and f1, however in strobing mode the scheme is repeated for all frames. When these frames are exposed for the maximum of one frame there is a small gap as shown separating the two frames, where the frame is not exposed depending on the specific configuration of the sensor, which is different for each sensor. This non-exposed area takes place at the end of the exposure of a line, as shown twice in the diagrams. The shift from one line to the other is due to the architecture of the rolling shutter, where each frame line is exposed with a small shift after each other rolling through the entire frame. The LED pulses shown at the bottom are timed based on the audio frequency of the patient's vocal cord to expose the vocal cord. Typically the pulses are strobed at a time interval inverse to the measured base frequency, as further discussed with regard to the process described below.

The diagram of FIG. 3 will be described further with reference to the process of FIG. 4, which shows a flowchart of a method for operating the stroboscopic scope system. At process block 402, the procedure is set up attaching the microphone to the patient's throat near the larynx, or setting it in another suitable location to detect vocalization. The scope is inserted into the patient's throat or nose to view the larynx, and the procedure begins.

Next at block 404, the process measures a patient's vocalization, made under direction of the examining technician or doctor, with the microphone. The exam typically includes the patient singing a variety of tones and making other vocalizations. At block 406, the CCU analyzes the audio data to determine the base frequency of the vocalization. This is typically done with a digital fast Fourier transforms (FFT) and frequency domain analysis of the result, for example to find the frequency with a maximum power level, or a local maximum, or other suitable frequency domain analysis. At block 408, the process selects a strobing frequency or time sequence for pulsing the strobe light of the scope based on the base frequency of the vocalization. Typically the strobe timing is determined directly from the base frequency f, to perform strobing at 1/f, however this is not limiting and different procedures may analyze other characteristics besides the base frequency, and select appropriate strobing sequences accordingly.

At block 410, the process, on a continuous basis while observing the patient's vocal cords with the stroboscopic laryngoscope during the patient's vocalization, pulses the light emitter of the stroboscopic laryngoscope at time intervals selected based on the base frequency of the vocalization. Such pulses are seen in FIG. 2, where pulses p0-p4 are timed at the inverse of the base frequency (the separation time of the pulses is 1/f where f is the measure base frequency). As shown at block 410, the sequence of pulses is chosen such that two adjacent frames are exposed with at least two pulses. Often more pulses than the four depicted are used, for example at a frame rate of 30 fps, with a typical adult voice having a lowest base or fundamental frequency from 85 to 180 Hz for men and 165 to 255 Hz for women, and much higher base frequencies as the vocalization pitch increases, at higher base frequencies several pulses will occur in each frame. The duty cycle of the time period of such a strobe pulse may be less than 100%.

Next at block 412 the process includes reading image data from the image sensor array of the stroboscopic laryngoscope according to a rolling shutter process. In the depicted version of FIG. 2, the rolling shutter process reads the image data from lines of the image sensor array, each line of the frames f0 and f1 offset in time such that at least two of the two or more light emitter pulses each expose sensor pixels in both first and second adjacent frames simultaneously.

FIG. 3 shows the use of the data in constructing a new combined frame. This is done in FIG. 4, process block 414, where the process selects a first subset of the image sensor data from the first frame and a second subset of the image sensor data from the second frame. The subsets are selected as shown at block 416 with the second subset including a different frame portion than the first subset, the first and second subsets including data resulting from the simultaneous exposure of the first and second frames. An example of this is shown in FIG. 3, where the first subset of data out of frame F0 is shown labeled as A1, including data from the second half of the array in this version. The second subset A2 is shown selected out of the second frame F1, where the second subset of data is from the first half of the array.

Preferably, the image sensor is set to the maximum exposure of one frame minus the gap where it cannot be exposed. As the CCU has control over the light source, light pulses are prohibited outside the time window of A1 and A2, as can be seen in FIG. 3 where the pulses p0 and p4 are omitted (as shown by the X over the depicted pulse) from the regular sequence of pulses for the depicted two frames. The gap of time in which the lines are not exposed leads to non equal exposure of lines among the frame. For example, the timing of P2 is such that the scan of line 5 (f0, I5 and f1, I5) is not exposed by pulse p2, and therefore the process includes applying a gain adjustment to the data of line 5. Similarly pulse P3 may fall in the game for line 8, and adjustment may be applied. In order to accomplish such adjustment, the CCU keeps track of when the frame line is not exposed, e.g., during the gap, and the LED creates a light pulse for a certain period of time for each frame line. When the two frames are combined at block 418, the CCU preferably compensates for this loss of exposure by adding a specific digital gain to each frame line. If this is not done, a pattern would be seen of less and more exposed lines among the frame.

As can be seen on the diagrams of FIG. 2 and FIG. 3, a rolling shutter type array has the disadvantage that a single strobe in each frame does not provide sufficient exposure for all lines to be exposed and read for a single frame. In the depicted process, in order to have an exposure that is longer than only one frame minus the exposure gap, subsets from two frames are added together. This provides a virtual longer exposure and new virtual frame rate of half of the real frame rate coming out of the image sensor. Referring again to FIG. 4, at block 418 the process combines the image sensor data from the first and second subsets A1 and A2 to create a combined frame based on the first and second frames. The CCU feeds the combined frame to the display as part of a video feed, and may also record the video feed to non-transitory memory.

Then the process returns to block 406 where it continuously updates the base frequency employed in determining the strobe rate and continues to process the next frame of images for a video stream. As can be seen in FIG. 3, the first and second subsets of image data A1 and A2 can be selected out of a continuous series of frames one after the other. In a preferred version, the two adjacent frames f0 and f1 as shown are exposed with the depicted pulses, with the subsets of data extracted and combined to form a single frame, and the remaining data (in this version, the depicted data not inside the shaded areas of A1 and A2) is discarded. This produces one display frame for every two scanned frames from the image sensor, effectively halving the frame rate from the sensor. For example, a 60 fps sensor would produce a 30 fps video stream with such a method. Typically the CCU would still drive the display with the refresh rate of the display, which might be higher than half the frame rate of the image sensor. The next frame in the series of FIG. 3 would be a combination based on f2 and f3, not f1 and f2, because the frame rate would have to align evenly to build again a full frame out of two half frames, without influencing or exposing the previous sequence of frame f0 and f1. It is noted that the process only adjusts the base frequency after processing two frames for combination, such that the combined frames are illuminated strobed at the same frequency.

As can be understood, for subsequent frames the process includes creating subsequent two or more light emitter pulses for subsequent image frames spaced in time from the pulses of the first and second image frames according to integer multiples of a time period that is the inverse of the base frequency of the vocalization. The process may further include adjusting a digital gain applied to the image data based on how many pulses of light are employed in exposing each particular line of the rolling shutter readout in the subsequent frames, given that the relative location of the pulses within the subsequent frames will change over time. If the base frequency of the vocalization changes over time, the time period is adjusted to the inverse of the new frequency, but only applied to the consecutive pair of two frames.

As can be seen in the example version of FIG. 3, the first subset A1 includes only data scanned in a second-half period of reading the first frame, and the second subset A2 includes only data scanned in a first-half period of reading the second frame. It is understood that the halves may share a bordering image sensor array line such as the depicted line L5 from which is read data for both subsets, in different frames.

Between a pair of two consecutive combined frames, a slight offset or phase delay to the time interval of the pulses may be made to allow the vocal cord position to be slightly offset between a pair of frames, causing the sequence of frames to appear as slow-motion movement typical of laryngeal stroboscopy.

As can be understood, the process described allows a stroboscopic analysis of vocal cords synchronized in frequency to be performed with a rolling shutter type image array, instead of being limited to a global exposure type shutter arrangement. It is assumed that the camera head or videoendoscope is not moved during this stroboscopy mode, because this would lead to smearing of the image.

Because digital cameras and stroboscopic devices and related circuitry for signal capture and processing are well-known, the present description will be directed in particular to elements forming part of, or cooperating more directly with, a method and apparatus in accordance with the invention. Elements not specifically shown or described herein are selected from those known in the art. Certain aspects of the embodiments to be described are provided in software. Given the system as shown and described according to the invention in the following materials, software not specifically shown, described or suggested herein that is useful for implementation of the invention is conventional and within the ordinary skill in such arts.

Figure 5:
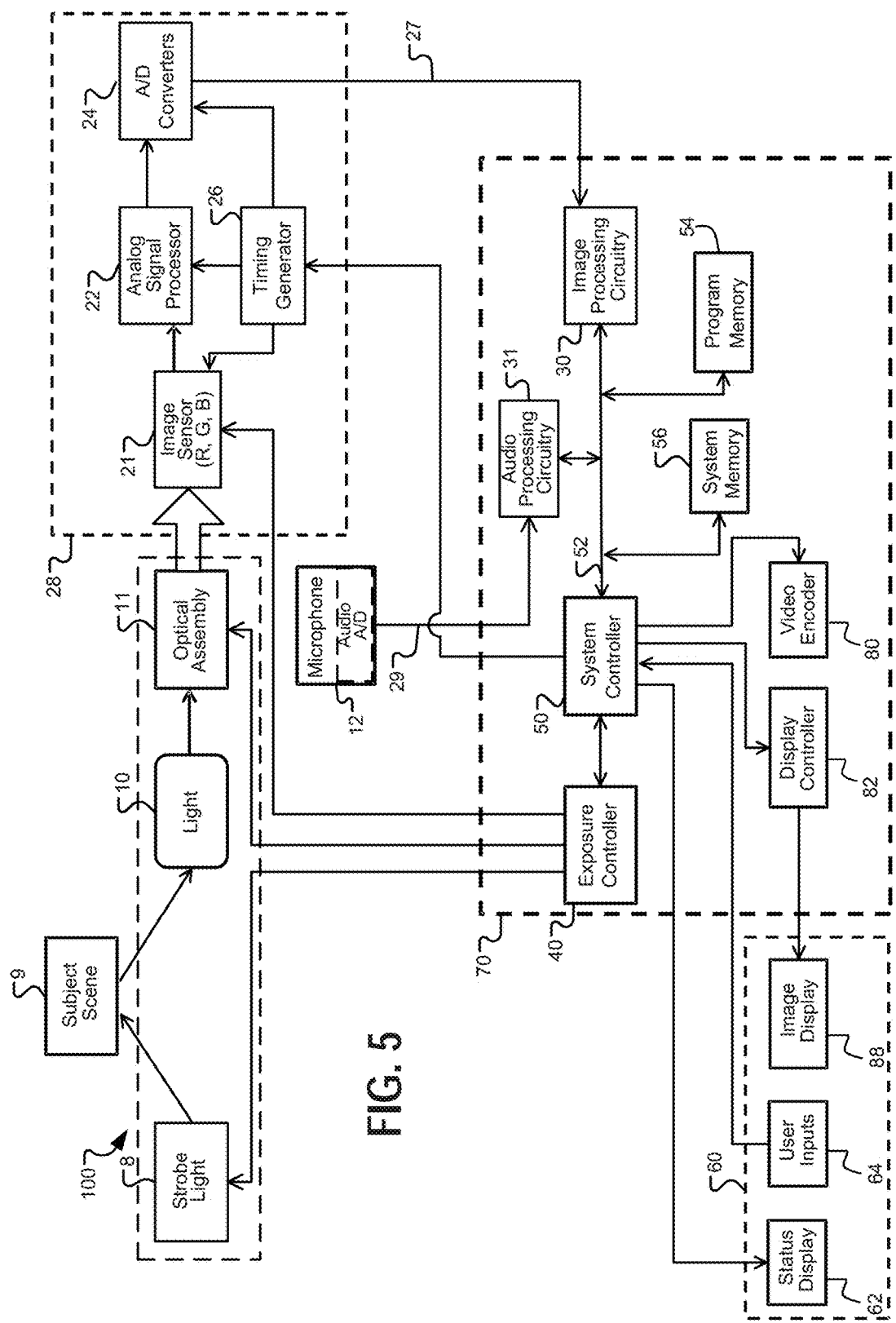
FIG. 5 is a hardware block diagram of an example system including a medical scope, a camera control module, and an electronic display.

Referring to FIG. 5, shown is a system hardware block diagram of an example system including a medical scope 100, a camera control module 70, and a user interface 60 including one or more displays, the system being one example hardware design on which the laryngeal stroboscopy techniques described herein may be implemented. The medical scope 100 in this system is a dual mode stroboscopic laryngoscope with a continuous light mode and a strobing light mode, however this is not limiting and the features and techniques herein that may be employed with other stroboscopic endoscopes. Of the depicted blocks, scope 100 includes the optical assembly 11 and the camera head and handle 28 ("camera head", "handle") which may be detachable from the scope shaft or may be integrated with the shaft as in the scope of FIG. 1. The scope may also include the light source 8, preferably an LED light source positioned at the tip of the scope shaft such that it illuminates the vocal cords when in inserted in a position like that of FIG. 1.

The light source 8, typically an LED emitter, illuminates subject scene 9. Light source 8 may include a single or multiple light emitting elements configured to provide light throughout the desired spectrum. Further, light source 8 may include fiber optics passing through the body of the scope, or other light emitting arrangements such as LEDs or laser diodes positioned at or near the front of the scope. The light source may also be an external light source or part of the CCU 70, which provides the light for rigid endoscopes. As shown in the drawing, light 10 reflected from the subject scene is passed to an optical assembly 11, where the light is focused toward an image sensor assembly to form an image at a solid-state image sensor(s) 21. Optical assembly 11 includes at least one lens, which may be a wide-angle lens element such that optical assembly 11 focuses light which represents a wide field of view. Portions of the optical assembly may be embodied in a camera head 28, while other portions are in an endoscope shaft. In some embodiments of the invention, the scope handle 28 contains control electronics but the image sensor(s) is located in the scope shaft itself, often toward the distal end of the shaft. The optical assembly 11 may be contained in a single imaging device with the image sensor assembly. Image sensor 21 (convert the incident light to an electrical signal by integrating charge for each picture element (pixel). The image sensor 21 may be active pixel complementary metal oxide semiconductor active pixel sensor (CMOS APS) or a charge-coupled device (CCD), or other suitable image sensor.

Timing generator 26 produces various clocking signals to select rows and pixels and synchronizes the operation of image sensor 21 and analog signal processor 22, and A/D converter 24 according to the timing described above with regard to FIGS. 2-4. The image sensor assembly typically includes the image sensor 21, the analog signal processor 22, the A/D converter 24, and the timing generator 26. The functional elements of the image sensor assembly can be fabricated as a single integrated circuit as is commonly done with CMOS image sensors or they can be separately-fabricated integrated circuits.

The total amount of light 10 reaching the image sensor 21 is regulated by the light source 8 intensity, the optical assembly 11 aperture, the time for which the image sensor 21 integrates charge and the number of strobe pulses dependent on the vocal cord base frequency in stroboscopy mode.

An exposure controller 40 responds to the amount of light available in the scene given the intensity and spatial distribution of digitized signals corresponding to the intensity and spatial distribution of the light focused on image sensor 222.

Analog signals from the image sensor 21 are processed by analog signal processor 22 and applied to analog-to-digital (A/D) converter 24 for digitizing the analog sensor signals. The digitized signals each representing streams of images or image representations based on the data, are fed to image processor 30 as image signal 27.

Figure 4:
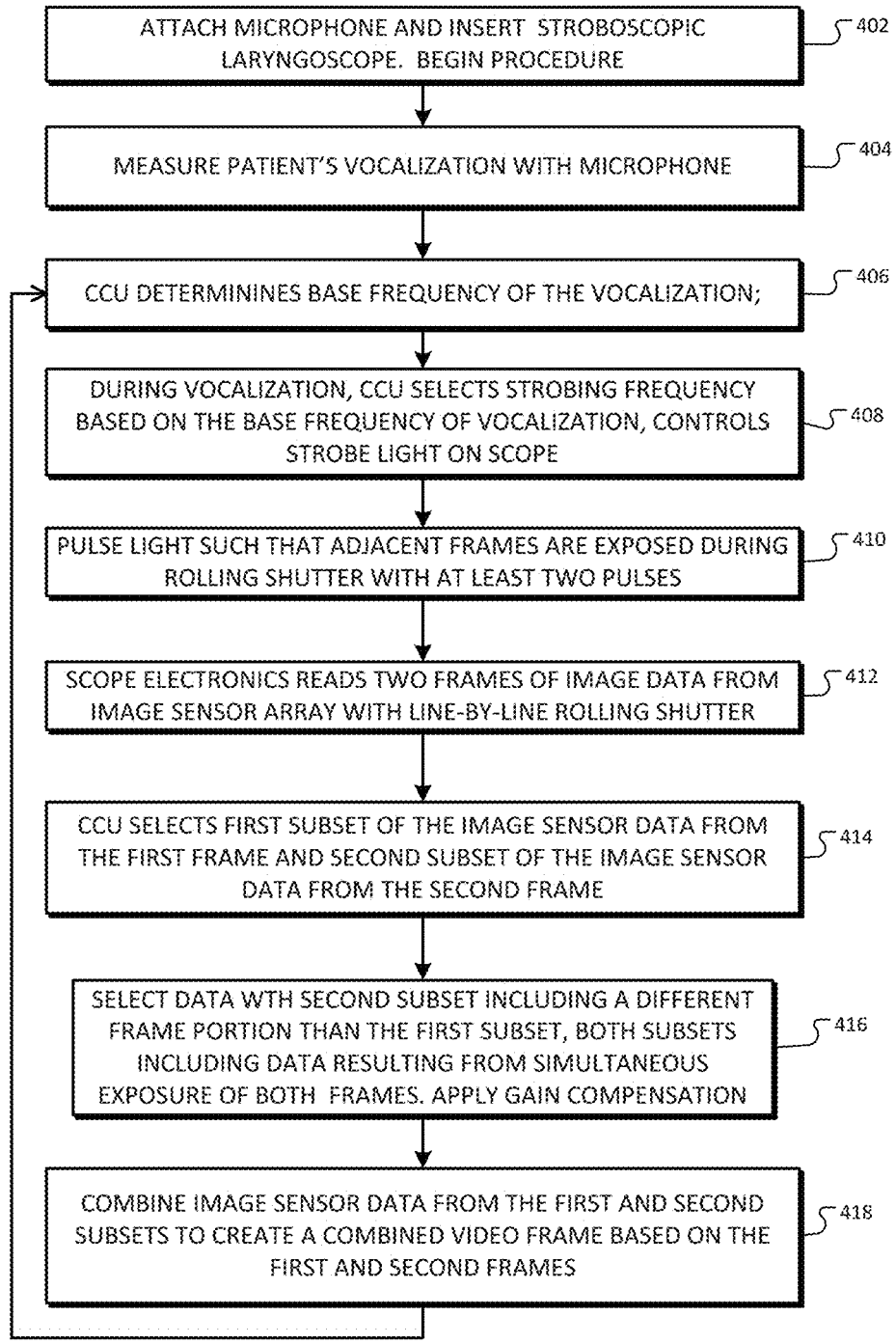
FIG. 4 shows a flowchart of a process for controlling a stroboscopy system and processing data therefrom.

Image processing circuitry 30 includes circuitry for extracting the subsets of image data as described according to the process of FIG. 4, and combining the image data subsets to create combined image frames. This may be done in programmable hardware or in one or more digital signal processing cores programmed with suitable firmware. Image processing circuitry 30 preferably includes a gain processing module that applies a digital gain to values on one or more lines in the first and second subsets to compensate for a loss of exposure due to a time gap between the first and second adjacent frames according to the processes described herein. Image processing circuitry 30 also includes circuitry performing digital image processing functions to process and filter the received images as is known in the art.

Audio processing circuitry 31 receives the audio signal from microphone 12, which in use is positioned on or near the patient. The microphone may include an A/D converter to digitize the audio signal or such conversion may be made by the CCU audio processing circuitry 31. Typically the audio processing circuitry is implemented in either a DSP or FPGA/coprocessor arrangement, and performs digital fast Fourier transforms (FFT) and frequency domain analysis in order to measure the audio power levels at each frequency in the audio signal and determine the base frequency of the patient vocalization. Such circuitry is known in the art of stroboscopic laryngoscopes and will not be further described. Typically audio processing circuitry 31 is implemented on the same device as image processing circuitry 30.

The system controller 50 controls the overall operation of the image capture device based on a software program stored in program memory 54. This memory can also be used to store user setting selections and other data to be preserved when the camera is turned off. System controller 50 controls the sequence of data capture by directing exposure controller 40 to set the light source 8 intensity, control the pulsing of light source 8 when in strobing mode, and control the optical assembly 11 aperture, and controlling various filters in optical assembly 11 and timing that may be necessary to obtain the image stream. A data bus 52 includes a pathway for address, data, and control signals.

Processed image data are continuously sent to video encoder 80 to store data for later review of the procedure by the user. The processed image data is also formatted by display controller 82 and presented on image display 88. This display is typically a liquid crystal display backlight with light-emitting diodes (LED LCD), although other types of displays are used as well. The processed image data can also be stored in system memory 56 or other internal or external memory device.

The user interface 60, including all or any combination of image display 88, user inputs 64, and status display 62, is controlled by a combination of software programs executed on system controller 50, receiving input from user inputs 64 and from buttons positioned on the scope handle. User inputs 64 typically include some combination of typing keyboards, computer pointing devices, buttons, rocker switches, joysticks, rotary dials, or touch screens. The system controller 50 manages the graphical user interface (GUI) presented on one or more of the displays (e.g. on image display 88). In particular, the system controller 50 will typically have a mode toggle user input (typically through a configurable button on the endoscope or camera head itself, but possibly through a GUI interface), and in response transmit commands to adjust image processing circuitry 30 based on predetermined setting stored in system memory. Preferably a system employed with any of the device designs herein provides ability to toggle between at least two modes, continuous light mode and strobing mode.

Image processing circuitry 30 is one of three programmable logic devices, processors, or controllers in this embodiment, in addition to a system controller 50 and the exposure controller 40. Image processing circuitry 30, controller 50, exposure controller 40, system and program memories 56 and 54, video encoder 80 and display controller 82 may be housed within camera control unit (CCU) 70.

CCU 70 may be responsible for powering and controlling light source 8, the image sensor assembly, and/or optical assembly 11, and may power and receive signals directly from the buttons on the scope 100, or indirectly if the buttons pass their signals through a controller in the camera head such as the analog signal processor. Such power and control connections are not depicted separately but will typically be contained in a single flexible cable with data connection 27.

Although this distribution of imaging device functional control among multiple programmable logic devices, processors, and controllers is typical, these programmable logic devices, processors, or controllers can be combinable in various ways without affecting the functional operation of the imaging device and the application of the invention. These programmable logic devices, processors, or controllers can comprise one or more programmable logic devices, digital signal processor devices, microcontrollers, or other digital logic circuits. Although a combination of such programmable logic devices, processors, or controllers has been described, it should be apparent that one programmable logic device, digital signal processor, microcontroller, microprocessors or other digital logic circuit can be designated to perform all of the needed functions. All of these variations can perform the same function and fall within the scope of this invention.

As used herein the terms "comprising," "including," "carrying," "having" "containing," "involving," and the like are to be understood to be open-ended, that is, to mean including but not limited to. Any use of ordinal terms such as "first," "second," "third," etc., in the claims to modify a claim element does not by itself connote any priority, precedence, or order of one claim element over another, or the temporal order in which acts of a method are performed. Rather, unless specifically stated otherwise, such ordinal terms are used merely as labels to distinguish one claim element having a certain name from another element having a same name (but for use of the ordinal term).

The foregoing has outlined rather broadly the features and technical advantages of the invention in order that the detailed description of the invention that follows may be better understood. It should be appreciated by those skilled in the art that the conception and specific embodiments disclosed may be readily utilized as a basis for modifying or designing other structures for carrying out the same purposes of the invention. It should also be realized by those skilled in the art that such equivalent constructions do not depart from the scope of the invention as set forth in the appended claims.

Although the invention and its advantages have been described in detail, it should be understood that various changes, substitutions and alterations can be made herein without departing from the scope of the invention as defined by the appended claims. The combinations of features described herein should not be interpreted to be limiting, and the features herein may be used in any working combination or sub-combination according to the invention. This description should therefore be interpreted as providing written support, under U.S. patent law and any relevant foreign patent laws, for any working combination or some sub-combination of the features herein.

Moreover, the scope of the present application is not intended to be limited to the particular embodiments of the process, machine, manufacture, composition of matter, means, methods and steps described in the specification. As one of ordinary skill in the art will readily appreciate from the disclosure of the invention, processes, machines, manufacture, compositions of matter, means, methods, or steps, presently existing or later to be developed that perform substantially the same function or achieve substantially the same result as the corresponding embodiments described herein may be utilized according to the invention. Accordingly, the appended claims are intended to include within their scope such processes, machines, manufacture, compositions of matter, means, methods, or steps.

The invention claimed is:

1. A medical scope system comprising:
a stroboscopic laryngoscope;
a microphone;
a camera control module including an electronic controller communicatively coupled to the stroboscopic laryngoscope and the microphone;
a display device communicatively coupled to the camera control module; and
wherein the camera control module electronic controller is operable for:
measuring a patient's vocalization with the microphone and determining a base frequency of the vocalization;
during the patient's vocalization, causing a light emitter of the stroboscopic laryngoscope to pulse at a timing interval selected based on the base frequency of the vocalization;
reading image data from an image sensor array of the stroboscopic laryngoscope according to a rolling shutter process including: (a) creating two or more light emitter pulses during first and second adjacent image frames, (b) reading the image data from lines of the image sensor array offset in time such that at least two of the two or more light emitter pulses each expose sensor pixels in both first and a second image frames simultaneously, and (c) selecting a first subset of the image data from the first frame and a second subset of the image sensor data from the second frame, the second subset including a different frame portion than the first subset, the first and second subsets including data resulting from the simultaneous exposure of the first and second frames;
combining the image data from the first and second subsets to create a combined image frame based on the first and second frames; and
applying a digital gain to values on one or more lines in the first and second subsets to compensate for a loss of exposure due to a gap time between the first and second frames in the rolling shutter process.

2. The system of claim 1, in which the first subset includes only data scanned in a second-half period of reading the first frame, and the second subset includes only data scanned in a first-half period of reading the second frame.

3. The system of claim 1, in which the camera control module is further operable for repeating (a)-(c) for subsequent pairs of image frames following the first and second image frames and combining image data from subsequent first and second subsets into subsequent combined image frames.

4. The system of claim 3, in which the camera control module is further operable for creating subsequent two or more light emitter pulses for subsequent image frames spaced in time from the pulses of the first and second image frames according to integer multiples of a time period that is the inverse of the base frequency of the vocalization.

5. The system of claim 1, in which the camera control module is further operable for creating the two or more light emitter pulses in a sequence in which the pulses are spaced at a time period that is the inverse of the base frequency of the vocalization, and in which a gap occurs in the sequence such that at least one pulse is missing.

6. A method of operating a medical scope system, the method comprising:
measuring a patient's vocalization with a microphone and determining a base frequency of the vocalization;
observing the patient's vocal cords with a stroboscopic laryngoscope during the patient's vocalization and pulsing a light emitter of the stroboscopic laryngoscope or an associated camera control unit at time intervals selected based on the base frequency of the vocalization;
reading image data from an image sensor array of the stroboscopic laryngoscope according to a rolling shutter process including: (a) creating two or more light emitter pulses during two consecutive video frames, (b) reading the image data from lines of the image sensor array offset in time such that at least two of the two or more light emitter pulses each expose sensor pixels in both first and second adjacent frames simultaneously, and (c) selecting a first subset of the image sensor data from the first frame and a second subset of the image sensor data from the second frame, the second subset including a different frame portion than the first subset, the first and second subsets including data resulting from the simultaneous exposure of the first and second frames;
combining the image sensor data from the first and second subsets to create a combined frame based on the first and second frames; and
applying a digital gain to values on one or more lines in the first and second subsets to compensate for a loss of exposure due to a gap time between the first and second frames in the rolling shutter process.

7. The method of claim 6, in which the first subset includes only data scanned in a second-half period of reading the first frame, and the second subset includes only data scanned in a first-half period of reading the second frame.

8. The method of claim 6, further comprising repeating (a)-(c) for subsequent pairs of image frames following the first and second image frames and combining image data from subsequent first and second subsets into subsequent combined image frames.

9. The method of claim 8, further comprising creating subsequent two or more light emitter pulses for subsequent image frames spaced in time from the pulses of the first and second image frames according to integer multiples of a time period that is the inverse of the base frequency of the vocalization.

10. The method of claim 6, further comprising creating the two or more light emitter pulses in a sequence in which the pulses are spaced at a time period that is the inverse of the base frequency of the vocalization, and in which a gap occurs in the sequence such that at least one pulse is missing.

11. A camera control module for use with a stroboscopic laryngoscope, the camera control module comprising:
an electronic controller adapted to communicatively couple to a stroboscopic laryngoscope, a display device, and a microphone, the camera control module electronic controller is operable for:
receiving an audio signal patient's vocalization with the microphone and determining a base frequency of the vocalization;
commanding a light emitter of the stroboscopic laryngoscope to pulse at time intervals selected based on the base frequency of the vocalization;
reading image data from an image sensor array of the stroboscopic laryngoscope according to a rolling shutter process including: (a) creating two or more light emitter pulses during each video frame, (b) reading the image data from lines of the image sensor array offset in time such that at least two of the two or more light emitter pulses each expose sensor pixels in both first and second adjacent frames simultaneously, and (c) selecting a first subset of the image sensor data from the first frame and a second subset of the image sensor data from the second frame, the second subset including a different frame portion than the first subset, the first and second subsets including data resulting from the simultaneous exposure of the first and second frames;
combining the image sensor data from the first and second subsets to create a combined frame based on the first and second frames; and
applying a digital gain to values on one or more lines in the first and second subsets to compensate for a loss of exposure due to a gap time between the first and second frames in the rolling shutter process.

12. The camera control module of claim 11, in which the first subset includes only data scanned in a second-half period of reading the first frame, and the second subset includes only data scanned in a first-half period of reading the second frame.

13. The camera control module of claim 11, further operable for repeating (a)-(c) for subsequent pairs of image frames following the first and second image frames and combining image data from subsequent first and second subsets into subsequent combined image frames.

14. The camera control module of claim 13, in which the camera control module is further operable for creating subsequent two or more light emitter pulses for subsequent image frames spaced in time from the pulses of the first and second image frames according to integer multiples of a time period that is the inverse of the base frequency of the vocalization.

15. The camera control module of claim 11, in which the camera control module is further operable for creating the two or more light emitter pulses in a sequence in which the pulses are spaced at a time period that is the inverse of the base frequency of the vocalization, and in which a gap occurs in the sequence such that at least one pulse is missing.

* * * * *